United States Patent
Popescu et al.

(10) Patent No.: US 12,021,967 B2
(45) Date of Patent: Jun. 25, 2024

(54) PRIVACY PRESERVING ARTIFICIAL INTELLIGENCE BASED CLINICAL DECISION SUPPORT

(71) Applicant: SIEMENS HEALTHINEERS AG, Forchheim (DE)

(72) Inventors: Andreea Bianca Popescu, Constanta (RO); Cosmin Ioan Nita, Brasov (RO); Ioana Taca, Brasov (RO); Anamaria Vizitiu, Covasna (RO); Lucian Mihai Itu, Brasov (RO); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 309 days.

(21) Appl. No.: 17/449,463

(22) Filed: Sep. 30, 2021

(65) Prior Publication Data

US 2023/0044776 A1    Feb. 9, 2023

Related U.S. Application Data

(60) Provisional application No. 63/203,236, filed on Jul. 14, 2021.

(30) Foreign Application Priority Data

Jul. 14, 2021    (EP) ..................... 21465536

(51) Int. Cl.
*H04L 29/06*    (2006.01)
*G16H 50/20*    (2018.01)
*H04L 9/00*    (2022.01)

(52) U.S. Cl.
CPC ............. *H04L 9/008* (2013.01); *G16H 50/20* (2018.01)

(58) Field of Classification Search
None
See application file for complete search history.

(56) References Cited

U.S. PATENT DOCUMENTS

| | | | | |
|---|---|---|---|---|
| 10,075,288 | B1 * | 9/2018 | Khedr | ............... H04L 9/008 |
| 10,491,373 | B2 * | 11/2019 | Jain | ..................... H04L 9/008 |
| 10,554,390 | B2 * | 2/2020 | Jain | ....................... H04L 9/08 |
| 10,608,811 | B2 * | 3/2020 | Chen | ................... H04L 9/0861 |
| 11,005,661 | B1 * | 5/2021 | Neumann | ................ G06N 3/08 |
| 2016/0097716 | A1 * | 4/2016 | Gulati | ................. A61B 5/1495 |
| | | | | 250/340 |
| 2017/0293913 | A1 * | 10/2017 | Gulak | ............... G06Q 20/3829 |

(Continued)

OTHER PUBLICATIONS

Xin, Guozhu et al. A Multi-Layer Parallel Hardware Architecture for Homomorphic Computation in Machine Learning. 2021 IEEE International Symposium on Circuits and Systems (ISCAS). https://ieeexplore.ieee.org/stamp/stamp.jsp?tp=&arnumber=9401623 (Year: 2021).*

(Continued)

*Primary Examiner* — Jeremiah L Avery

(57) ABSTRACT

Data privacy is a major concern when accessing and processing sensitive medical data. Homomorphic Encryption (HE) is one technique that preserves privacy while allowing computations to be performed on encrypted data. An encoding method enables typical HE schemes to operate on real-valued numbers of arbitrary precision and size by representing the numbers as a series of polynomial terms.

16 Claims, 7 Drawing Sheets

(56) References Cited

U.S. PATENT DOCUMENTS

| | | | |
|---|---|---|---|
| 2019/0087689 A1* | 3/2019 | Chen | H04L 9/0825 |
| 2019/0158340 A1* | 5/2019 | Zhang | H04B 17/318 |
| 2019/0178980 A1* | 6/2019 | Zhang | A61B 5/7267 |
| 2020/0019867 A1* | 1/2020 | Nandakumar | G06N 3/048 |
| 2020/0104636 A1* | 4/2020 | Halevi | G06F 18/211 |
| 2020/0366459 A1* | 11/2020 | Nandakumar | H04L 9/008 |
| 2020/0403781 A1* | 12/2020 | Gentry | G06F 21/602 |
| 2021/0022676 A1* | 1/2021 | Lamego | A61B 5/369 |
| 2021/0133614 A1* | 5/2021 | Ashrafi | G06N 10/00 |
| 2021/0232940 A1* | 7/2021 | Dalli | G06N 3/08 |
| 2021/0314140 A1* | 10/2021 | Stephenson | H04L 9/3218 |

OTHER PUBLICATIONS

Li, Qifei et al. HomoPAI: A Secure Collaborative Machine Learning Platform based on Homomorphic Encryption. 2020 IEEE 36th International Conference on Data Engineering (ICDE). https://ieeexplore.ieee.org/stamp/stamp.jsp?tp=&arnumber=9101628 (Year: 2020).*

Aslett, Louis J.M. et al. Encrypted statistical machine learning: new privacy preserving methods. https://arxiv.org/abs/1508.06845v1 (Year: 2015).*

Gaid, Michael Lahzi et al. Secure Translation Using Fully Homomorphic Encryption and Sequence-to-Sequence Neural Networks. 2018 28th International Conference on Computer Theory and Applications (ICCTA). https://ieeexplore.ieee.org/stamp/stamp.jsp?tp=&arnumber=9499157 (Year: 2018).*

Arita, Seiko; Nakasato, Shota. Fully Homomorphic Encryption for Classification in Machine Learning. 2017 IEEE International Conference on Smart Computing (SMARTCOMP). https://ieeexplore.ieee.org/stamp/stamp.jsp?tp=&arnumber=7947011 (Year: 2017).*

Klemsa, Jakub; Novotny, Martin. WTFHE: neural-netWork-ready Torus Fully Homomorphic Encryption. 2020 9th Mediterranean Conference on Embedded Computing (MECO). https://ieeexplore.ieee.org/stamp/stamp.jsp?tp=&arnumber=9134331 (Year: 2020).*

Partial European Search Report mailed Mar. 3, 2022 in corresponding European Patent Application No. 21200152.3.

Joppe W Bos et al: "Private Predictive Analysis on Encrypted Medical Data"; International Association for Cryptologic Research; vol. May 15, 2014:063021; pp. 1-19.

Aslett, J. M. Louis et al: "Encrypted statistical machine learning: new privacy preserving methods"; Aug. 27, 2015.

Miotto, R.; Wang, F.; Wang, S.; Jiang, X.; Dudley, J.T. Deep learning for healthcare: Review, opportunities and challenges. Briefings Bioinform. 2018, 19, 1236-1246.

Shokri, R.; Shmatikov, V. Privacy-preserving deep learning. In Proceedings of the 22nd ACM SIGSAC Conference on Computer and Communications Security, Denver, CO, USA, Oct. 12-16, 2015; pp. 1310-1321.

Mohassel, P.; Zhang, Y. Secureml: A system for scalable privacy-preserving machine learning. In Proceedings of the 2017 IEEE Symposium on Security and Privacy (SP), San Jose, CA, USA, May 22-26, 2017; pp. 19-38.

McMahan, H.B.; Ramage, D.; Talwar, K.; Zhang, L. Learning differentially private recurrent language models. arXiv 2017, arxiv:1710.06963.

Phan, N.; Wang, Y.; Wu, X.; Dou, D. Differential privacy preservation for deep auto-encoders: an application of human behavior prediction. In Proceedings of the AAAI Conference on Artificial Intelligence, Phoenix, AZ, USA, Feb. 12-17, 2016; vol. 30.

Abadi, M.; Chu, A.; Goodfellow, I.; McMahan, H.B.; Mironov, I.; Talwar, K.; Zhang, L. Deep learning with differential privacy. In Proceedings of the 2016 ACM SIGSAC Conference on Computer and Communications Security, Vienna, Austria, Oct. 24-28, 2016; pp. 308-318.

Orlandi, C.; Piva, A.; Barni, M. Oblivious neural network computing via homomorphic encryption. EURASIP J. Inf. Secur. 2007, 2007, 1-11.

Gilad-Bachrach, R.; Dowlin, N.; Laine, K.; Lauter, K.; Naehrig, M.; Wernsing, J. Cryptonets: Applying neural networks to encrypted data with high throughput and accuracy. In Proceedings of the International Conference on Machine Learning, New York, NY, USA, Jun. 20-22, 2016; pp. 201-210.

Bos, J.W.; Lauter, K.; Loftus, J.; Naehrig, M. Improved security for a ring-based fully homomorphic encryption scheme. In Proceedings of the IMA International Conference on Cryptography and Coding, Oxford, UK, Dec. 17-19, 2013; pp. 45-64.

Hesamifard, E.; Takabi, H.; Ghasemi, M. Cryptodl: Deep neural networks over encrypted data. arXiv 2017, arxiv:1711.05189.

Fan, J.; Vercauteren, F. Somewhat practical fully homomorphic encryption. IACR Cryptol. ePrint Arch. 2012, 2012, 144.

Cheon, J.H.; Kim, A.; Kim, M.; Song, Y. Homomorphic encryption for arithmetic of approximate Nos. In Proceedings of the International Conference on the Theory and Application of Cryptology and Information Security, Hong Kong, China, Dec. 3-7, 2017; pp. 409-437.

Paillier, P. Public-key cryptosystems based on composite degree residuosity classes. In Proceedings of the International conference on the theory and applications of cryptographic techniques, Prague, Czech Republic, May 2-6, 1999; pp. 223-238.

Elgamal, T. A public key cryptosystem and a signature scheme based on discrete logarithms. IEEE Trans. Inf. Theory 1985, 31, 469-472.

Chen, H.; Laine, K.; Player, R.; Xia, Y. High-precision arithmetic in homomorphic encryption. In Proceedings of the Cryptographers' Track at the RSA Conference, San Francisco, CA, USA, Apr. 16-20, 2018; pp. 116-136.

Chen, H.; Laine, K.; Player, R. Simple encrypted arithmetic library-SEAL v2. 1. In Proceedings of the International Conference on Financial Cryptography and Data Security, Sliema, Malta, Apr. 3-7, 2017; pp. 3-18.

Fouque, P.A.; Stern, J.; Wackers, G.J. Cryptocomputing with rationals. In Proceedings of the International Conference on Financial Cryptography, Southampton, Bermuda, Mar. 11-14, 2002; pp. 136-146.

Moon, S.; Lee, Y. An efficient encrypted floating-point representation using HEAAN and TFHE. Secur. Commun. Netw. 2020, 2020, 1250295.

Jäschke, A.; Armknecht, F. Accelerating homomorphic computations on rational numbers. In Proceedings of the International Conference on Applied Cryptography and Network Security, London, UK, Jun. 19-22, 2016; pp. 405-423.

Liu, Y.; Huang, H.; Xiao, F.; Malekian, R.; Wang, W. Classification and recognition of encrypted EEG data based on neural network. J. Inf. Secur. Appl. 2020, 54, 102567.

Ahmad, M.; Farooq, O.; Datta, S.; Sohail, S.S.; Vyas, A.L.; Mulvaney, D. Chaos-based encryption of biomedical EEG signals using random quantization technique. In Proceedings of the 2011 4th International Conference on Biomedical Engineering and Informatics (BMEI), Shanghai, China, Oct. 15-17, 2011; vol. 3, pp. 1471-1475.

Xiang, G.; Chen, X.; Zhu, P.; Ma, J. A method of homomorphic encryption. Wuhan Univ. J. Nat. Sci. 2006, 11, 181-184.

Sathya, S.S.; Vepakomma, P.; Raskar, R.; Ramachandra, R.; Bhattacharya, S. A review of homomorphic encryption libraries for secure computation. arXiv 2018, arxiv:1812.02428.

Babyak, M.A. What you see may not be what you get: A brief, nontechnical introduction to overfitting in regression-type models. Psychosom. Med. 2004, 66, 411-421.

Alomari, M.H.; AbuBaker, A.; Turani, A.; Baniyounes, A.M.; Manasreh, A. EEG mouse: A machine learning-based brain computer interface. Int. J. Adv. Comput. Sci. Appl. 2014, 5, 193-198.

Shenoy, H.V.; Vinod, A.P.; Guan, C. Shrinkage estimator based regularization for EEG motor imagery classification. In Proceedings of the 2015 10th International Conference on Information, Communications and Signal Processing (ICICS), Singapore, Dec. 2-4, 2015; pp. 1-5.

Pedregosa, F.; Varoquaux, G.; Gramfort, A.; Michel, V.; Thirion, B.; Grisel, O.; Blondel, M.; Prettenhofer, P.; Weiss, R.; Dubourg, V.; et al. Scikit-learn: Machine Learning in Python. J. Mach. Learn. Res. 2011, 12, 2825-2830.

(56) References Cited

OTHER PUBLICATIONS

Andrzejak, R.G.; Lehnertz, K.; Mormann, F.; Rieke, C.; David, P.; Elger, C.E. Indications of nonlinear deterministic and finitedimensional structures in time series of brain electrical activity: Dependence on recording region and brain state. Phys. Rev. E 2001, 64, 061907.

Snodgrass, J.G.; Vanderwart, M. A standardized set of 260 pictures: Norms for name agreement, image agreement, familiarity, and visual complexity. J. Exp. Psychol. Hum. Learn. Mem. 1980, 6, 174.

Sun, Y.; Ye, N.; Xu, X. Eeg analysis of alcoholics and controls based on feature extraction. In Proceedings of the 2006 8th International Conference on Signal Processing, Guilin, China, Nov. 16-20, 2006; vol. 1.

Arita, S.; Nakasato, S. Fully homomorphic encryption for point numbers. In Proceedings of the International Conference on Information Security and Cryptology, Beijing, China, Nov. 4-6, 2016; pp. 253-270.

Dowlin, N.; Gilad-Bachrach, R.; Laine, K.; Lauter, K.; Naehrig, M.; Wernsing, J. Manual for using homomorphic encryption for bioinformatics. Proc. IEEE 2017, 105, 552-567.

Gentry, C., & Halevi, S. (May 2011). Implementing gentry's fully-homomorphic encryption scheme. In Annual International conference on the theory and applications of cryptographic techniques (pp. 129-148). Springer, Berlin, Heidelberg.

Jaschke, Angela, and Frederik Armknecht. "(Finite) field work: Choosing the best encoding of numbers for FHE computation." International Conference on Cryptology and Network Security. Springer, Cham, 2017. pp. 1-45.

\* cited by examiner

PRIVACY PRESERVING ARTIFICIAL INTELLIGENCE BASED CLINICAL DECISION SUPPORT

PRIORITY CLAIM

This application claims priority to U.S. provisional application Ser. No. 63/203,236, filed Jul. 14, 2021, and European Patent Application EP21465536, filed Jul. 14, 2021, both of which are entirely incorporated by reference.

FIELD

The following disclosure relates to artificial intelligence for clinical decision making.

BACKGROUND

Artificial intelligence (AI) is used in the medical domain to improve clinical decisions, increase patient safety, and reduce costs. Despite delivering promising results in personalized and/or precision medicine applications, AI approaches require proper anonymization in order to access sensitive data while respecting patient privacy. More effective privacy-preserving techniques may ensure compliance with regulations regarding personal data confidentiality (e.g. GDPR in the EU, HIPAA in the USA).

Encrypting patient data is one way to protect patient privacy. However, some encrypted data may be unsuitable for analysis. Homomorphic encryption (HE) is an encryption technique that allows data to be encrypted while retaining the ability to perform arithmetic operations on the encrypted data.

SUMMARY

By way of introduction, the preferred embodiments described below include methods, systems, instructions, and computer readable media for assessing medical data using a machine-learned model while keeping patient data private. Machine-learned models may analyze encrypted medical data and provide the result of the analysis, thus preserving privacy.

In a first aspect, a method for performing machine-learning tasks on medical data is provided. The method includes receiving, by a processor, medical data, encoding, by the processor, the medical data into encoded medical data according to an encoding scheme, wherein the encoding scheme represents a number in the medical data as a series of polynomial terms, encrypting, by the processor, the encoded medical data into encrypted medical data according to a homomorphic encryption scheme, applying, by the processor, the encrypted medical data to a machine-learned model, the machine learned model trained on second medical data, receiving, by the processor, an encrypted result generated by the machine-learned model based on applying the encrypted medical data to the machine-learned model, decrypting, by the processor, the encrypted result to an encoded result according to the homomorphic encryption scheme, decoding, by the processor, the encoded result to a medical data result according to the encoding scheme, and outputting, by the processor, the medical data result.

In one embodiment, the machine-learned model is cloud-based.

In one embodiment, a rational number is represented as the series of polynomial terms by the encoding scheme.

In one embodiment, each polynomial term comprises a sub-unity number and a power of ten.

In one embodiment, negative numbers in the medical data are represented by a difference between two polynomial terms.

In one embodiment, null digits of the number are unencoded by the encoding scheme.

In one embodiment, the method includes receiving, by the processor, a precision parameter. A number of the series of polynomial terms is based on the precision parameter.

In one embodiment, the medical data is encrypted with a cryptographic key used to encrypt the second medical data.

In a second aspect, a method for method of training a machine-learning model is provided. The method includes receiving, by a processor, training data comprising medical data and result data, wherein the medical data is annotated with corresponding result data, encoding, by the processor, the training into encoded training data according to an encoding scheme, wherein the encoding scheme represents a rational number as a series of polynomial terms, encrypting, by the processor, the encoded training data into encrypted training data according to a homomorphic encryption scheme, training with machine learning, by the processor, the machine-learning model based on the encrypted training data, wherein a result of the training is a machine-learned model configured to accept as input medical data and output result data, and wherein training further comprises: generating, by the processor, two matrices based on the encrypted training data, generating, by the processor, parameters of the machine-learning model based on the two matrices and a cost function comprising a linear system, and storing, by the processor, the machine-learned model.

In one embodiment, the method includes encoding, by the processor, the parameters of the machine-learning model into encoded parameters. The machine-learned model is stored with the encoded parameters.

In one embodiment, the homomorphic encryption scheme includes processing scalar operations.

In one embodiment, a result of the training is a machine-learned model configured to accept as input encrypted medical data and output encrypted result data.

In one embodiment, the training data is aggregated into a matrix form.

In one embodiment, the method includes receiving, by a processor, the medical data, encoding, by the processor, the medical data into encoded medical data according to the encoding scheme, encrypting, by the processor, the encoded medical data into encrypted medical data according to a homomorphic encryption scheme, applying, by the processor, the encrypted medical data to the machine-learned model, receiving, by the processor, encrypted result generated by the machine-learned model based on the encrypted medical data sent to the machine-learned model, decrypting, by the processor, the encrypted result to a encoded result according to the homomorphic encryption scheme, decoding, by the processor, the encoded result to a medical data result according to the encoding scheme, and outputting, by the processor, the medical data result.

In one embodiment, parameters of the machine-learned model, the encrypted medical data, and the encrypted training data are encrypted with the same encryption key.

In one embodiment, parameters of the machine-learned model are encoded according to the encoding scheme. The encrypted medical data is encrypted with a first key. The encrypted training data is encrypted with a second key different from the first key.

In a third aspect, a clinical assessment system is provided. The system includes a processor, coupled with a memory containing instructions that, when executed, cause the processor to send encoded-encrypted numerical data to a machine-learned model, receive an encoded-encrypted result generated by the machine-learned model based on the encoded-encrypted numerical data sent to the machine-learned model, decrypt the encoded-encrypted result to an encoded result according to the homomorphic encryption scheme, decode the encoded result to a numerical data result according to the encoding scheme, and output the numerical data result to the memory.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND EMBODIMENTS

Figure 1:
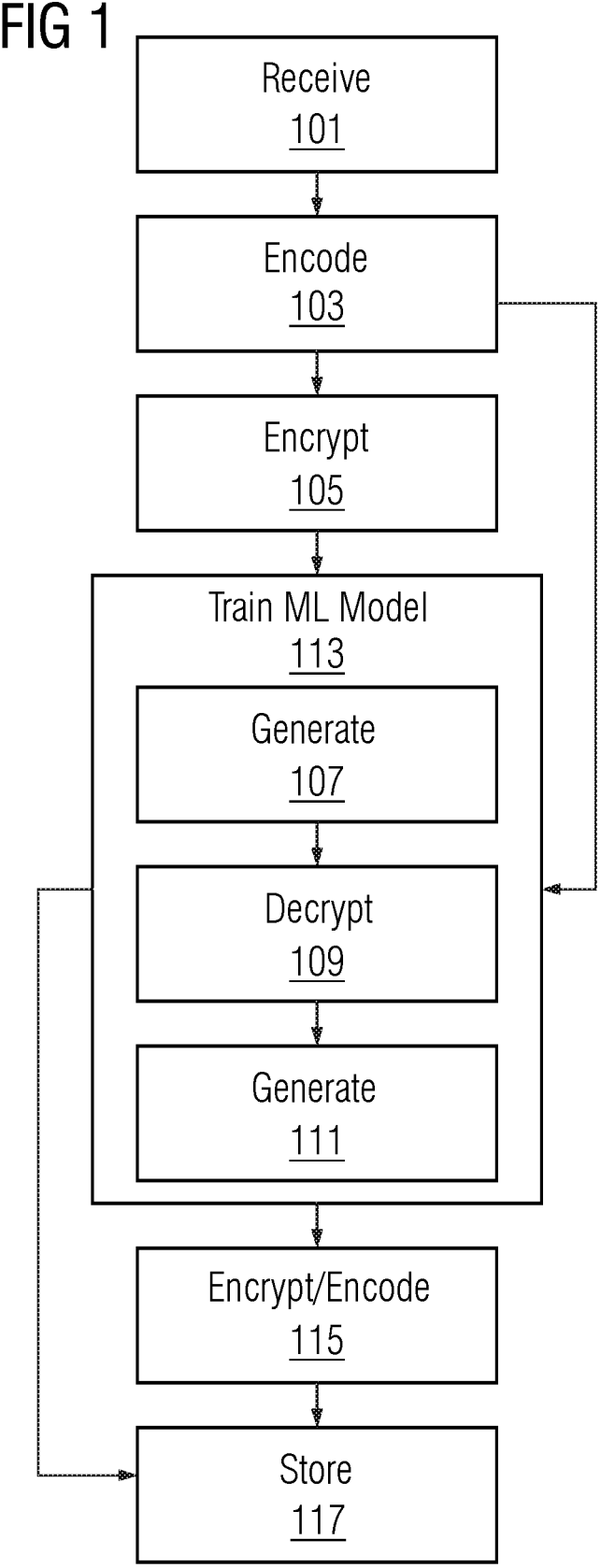
FIG. 1 illustrates an embodiment of a method of machine training a model for assessing medical images.

In recent years, privacy-preserving techniques have been developed that allow analysis of encrypted data. The analysis may be expanded to machine-learning-based analysis being performed on encrypted data. Techniques such as secure multiparty computation (SMPC), differential privacy and homomorphic encryption may be adopted in machine-learning applications. However, such techniques have limitations, leading to a trade-off between precision and privacy.

Starting with a first fully homomorphic encryption scheme, other schemes and implementation particularities have been proposed. Although the schemes ensure data security, many are homomorphic only for a limited number addition and multiplication operations on the encrypted data. Because of this limitation, surpassing the limit leads to difficulty in performing the decryption operation. Other schemes introduce noise over plaintext values, reducing the number of possible consecutive operations, and may be unable to encrypt real numbers. To overcome this limitation, other schemes may be used that affect the computational precision.

Homomorphic encryption schemes may be integrated in real-world medical applications that process real numbers. Multiple encoding methods that extend existing encryption schemes to real numbers may be used. In one example, an encoding technique that enables the use of the Paillier cryptosystem and corresponding homomorphic properties with rational numbers has been introduced, where a real value is written as a fraction of two integers. With this method, the numerator and denominator are bounded by a predefined domain and an additional step of decryption and approximation with smaller values is used to ensure that values remain between the imposed bounds.

In view of the above limitations, extension of homomorphic encryption schemes to real numbers may allow for the use of AI in clinical decision support applications. An approach allowing for the encryption and AI processing of real numbers is described. Encoding, encryption and optimization may be combined in a method that allows for AI model training and inference (e.g. analysis of medical data and generation of a result) on clinical real-valued data, ensuring at the same time data security and privacy preservation.

An encoding method is based on a polynomial representation of rational numbers where an encoded value is represented by a list of small integer pairs that may be readily encrypted using a HE scheme. Moreover, the method allows for a choice of the precision of the encoded rational values by selecting the number of terms in the polynomial representation. This way, the trade-off between computational accuracy and computational time may be controlled.

Although integrating homomorphic encryption schemes with encoding methods addresses some of the impediments that hinder real-world utility, there are still difficulties to be considered for obtaining an efficient encoding technique. As HE schemes are already complex, and encrypted operations require a higher computational cost than their plaintext equivalent, adding a new layer of encoding increases the complexity even more. Furthermore, expressing a value as a sequence of numbers leads to a ciphertext (data in an encrypted form) of growing size, as every number from the sequence is translated to its encrypted form. For example, when considering a polynomial representation, the multiplication of two encoded values results in an increased number of terms and in polynomials with a higher order. As the number of operations increases, the increasing dimension is more difficult to handle, and performing computations becomes more time consuming. To address the above problems, a polynomial representation of a number may use negative powers of 10, as described below.

FIG. 1 illustrates an embodiment of a method for training a machine-learning model for use with encoded and/or encrypted data. More, fewer, or different acts may be performed. In some cases, acts 115 and 117 may be omitted. A processor coupled to a memory may be configured to perform one or more of the acts. For example, the processor 703 of FIG. 7 may be configured to perform one or more of the acts of FIG. 1.

In act 101, input data, or training data, is received. The training data includes samples and corresponding ground truths. The input data may include two sets of numerical data. One set may be medical data, such as an EEG signal, or other data. The medical data may be annotated with information in the other set of numerical data. For example, the other set of numerical data may include a result of analysis on the medical data, such as a label (e.g., classification, segmentation, and/or detection). The first set of data may be annotated with corresponding entries in the second set of data. In the example of an EEG signal, the EEG signal may have a corresponding label in the second set of data, such as whether or not the signal represents a seizure.

The input data is aggregated in a matrix X, such that each row of the matrix represents an individual sample, and each element of the y output vector is the corresponding ground truth label (or other result for a particular clinical task) associated with each sample of the input data.

In act 103, the input data is encoded. When encoded, the input data (e.g. the matrix of medical data and the label or result data) may be referred to as "encoded data." A number of terms (e.g. a maximum number of terms) in the series of polynomial terms for encoding may be set based on the precision parameter.

To enable encryption of real numbers, the integer and the rational part are separated. Consider AER, a real number represented as $A = d_0, a_1, a_2 \ldots a_n$. All digits of the integer part, denoted by do, are encoded in the first coefficient of the polynomial, corresponding to 10 to the power of 0. The rational part is encoded differently, by multiplying each individual digit of the rational part with a negative power of 10, according to their position in the initial number. Zeroes in the rational part may be excluded from the terms. By adding these partial products, as in Equation (1) below, the encoding for a real value is a sequence of small integers. The n value denotes the number of decimals that are represented in this encoded representation. Based on a required precision for the application of the machine-learned model (e.g. classification, segmentation, simulation), the n value is set.

$$A = a_0 10^0 + a_1 10^{-1} + a_2 10^{-2} + \ldots + a_n 10^{-n} \quad (1)$$

The polynomial may also encrypt negative numbers by expressing each coefficient of the polynomial as a difference, as in Equation (2) below. If A is a negative number, then terms denoted by $a_0, a_1, a_2 \ldots a_n$ are equal to zero and the underlying information (e.g. digits) of the negative number is stored in the $b_0, b_1, b_2 \ldots b_n$ terms. This representation preserves the sign of A. A reference to a polynomial coefficient may designate a difference between polynomial representations, such as $(a_i - b_i)$.

$$A = (a_0 - b_0)10^0 + (a_1 - b_1)10^{-1} + (a_2 - b_2)10^{-2} + \ldots + (a_n - b_n)10^{-n} \quad (2)$$

For instance, $A = -13.8701$ may be encoded as follows:

$$-13.8701 = (0-13)10^0 + (0-8)10^{-1} + (0-7)10^{-2} + (0-1)10^{-4} \quad (3)$$

As discussed above and illustrated in Equation 3, null decimals of A are not present in the polynomial representation thereby simplifying the representation and allowing for an increase in precision. For example, for a given application, a precision requires five terms (n=5). Because the encoding considers only terms with non-zero decimals, more information from the original number is stored in the five terms of the polynomial representation of the original number.

Using this method, both positive and negative real numbers may be encoded with as many decimals as required for precision. Each coefficient may be encrypted by applying a HE scheme. As described with respect to at least equations (4a), (4b), (5), and 6, the operations that may be performed on the encoded and encrypted numbers are addition, subtraction, and multiplication. Homomorphic properties with respect to these operations are preserved by this encoding technique, being based on polynomial calculus.

For two real numbers $A_1$ and $A_2$, corresponding generic encoded representations are:

$$A_1 = (a_0 - b_0)10^0 + (a_1 - b_1)10^{-1} + (a_2 - b_2)10^{-2} + \ldots + (a_n - b_n)10^{-n} \quad (4a)$$

$$A_2 = (c_0 - d_0)10^0 + (c_1 - d_1)10^{-1} + (c_2 - d_2)10^{-2} + \ldots + (c_n - d_n)10^{-n} \quad (4b)$$

Addition is performed by adding the corresponding coefficients as in (5) below, while subtraction will consist in adding the opposite of the subtrahend that are computed, as in (6) below:

$$A_1 + A_2 = (a_0 + c_0 - (b_0 - d_0))10^0 + \ldots + (a_n + c_n - (b_n - d_n))10^{-n} \quad (5)$$

$$-A_2 = (d_0 - c_0)10^0 + (d_1 - c_1)10^{-1} + \ldots + (d_n - c_n)10^{-n} \quad (6)$$

To compute the product $A_1 \cdot A_2$, each coefficient of the first factor is multiplied with all coefficients of the second factor. The coefficients are grouped by the corresponding powers of ten. Multiplication of encoded real numbers may lead to an increase in the number of coefficients. Hence, the implementation of each operation allows for selecting a different number of decimals (n) to be stored in the result. The encoding process in act 103 may be limited by a precision parameter that may, in some cases, be received along with or separate from the medical data in act 101.

As is shown in equation (1), the entire integer part of a rational number is stored in a single coefficient, do. While the same value may be represented symmetrically by distributing individual digits of the integer part between different positive powers of 10 (e.g. $a_{-2}10^2 + a_{-1}10^1 + a_0 10^0 \ldots$), machine-learning-based techniques make use of data normalization, and all input numbers are normalized to sub-unitary numbers. Hence, adding more coefficients to the polynomial representation only to encode a zero value may lead to an avoidable computational overhead or loss in precision.

In act 105, the encoded input data (e.g. the matrix of encoded medical data and the encoded result data) are encrypted. A result of the encryption is encrypted medical data and encrypted result or label data. In some cases, because the encoded input data is encrypted, the output of the encryption may be referred to as encoded-encrypted data. The encryption may use a HE scheme. With the encoding method, any HE scheme that is homomorphic for addition and multiplication may be used, because these are the only two operations performed on ciphertexts during the encoded computations. Moreover, if a specific HE scheme enables scalar multiplication, the encoding method may also preserve this property. In this context, a scalar may be any integer that is neither encoded or encrypted, or any encoded (but not encrypted) real value.

The encoding act transforms the input rational number in a sequence of integers representing coefficients of a polynomial function. Each of the input coefficients may be encrypted using the HE scheme. The resulting ciphertext is also a sequence of integers. The encoding method does not affect the homomorphic properties of the ciphertext. An example encryption algorithm is described by Equation (7):

$$E_p(x) = s\,\mathrm{mod}((x + \mathrm{sign}(x) \cdot \mathrm{rand}(\ ) \cdot p), n) \quad (7)$$

In equation 7, x is the message (e.g. the coefficient after encoding) to be encrypted, p is a large prime number, and n is the product between p and another large prime number. The s mod operation is described in Equation (8), mod is the common modulo operation, rand yields a random positive integer, and the sign function provides the sign of x.

$$s\mathrm{mod}(m, p) = \begin{cases} \mathrm{mod}(m, p), & m \geq 0. \\ -(\mathrm{mod}(|m|, p)), & m < 0. \end{cases} \quad (8)$$

An example of a ciphertext obtained by encrypting the coefficients from the Equation (3) with this HE scheme, using a 32-bit key (for a simpler visualization), is represented in Equation (9).

$$-13.8701 = (19214182057 - 24703948372)10^0 + (8234649453 - 19214182065)10^{-1} + (13724415755 - 8234649460)10^{-2} + (5489766302 - 1097953260)10^{-4} \quad (9)$$

Training the machine-learning model in act 113 may include generating two matrices a matrix and a vector in act 107, decrypting the matrix and the vector, and/or generating regression coefficients. A result of the training may be a machine-learned model configured to accept data as an input (encrypted or decrypted) and output a result (encrypted or decrypted).

Numerical optimization may be performed using gradient-based iterative methods that converge in an unknown number of steps. Unfortunately, such formulations are difficult to apply on homomorphically encrypted data because they require an unknown (and typically large) number of operations, there are often nonlinear functions involved, and they require a comparison operation for evaluating the convergence. As most HE schemes are homomorphic only for addition and multiplication, they do not allow for division and do not support nonlinear function evaluation. The comparison between encrypted values is another operation that may be beyond the abilities of the HE scheme.

Alternatively, to bypass these challenges, optimization may be performed by approximating non-linear functions with low degree polynomials. Specifically, when performing such approximations, the resulting model turns into a polynomial function. If the loss function to be minimized is also analytically differentiable, the entire optimization problem is convex and may be solved analytically.

Let X be a N by M matrix containing the input data where each row xi is a data sample and y is a column vector of size N containing the output values.

Following the idea of encoding or encrypting the numbers into a polynomial form, the model function to be optimized may be reduced to a multivariate polynomial function as in Equation (10):

$$P(x) = \sum_{i=0}^{N_t} a_i p_i(x) \quad (10)$$

where pi(x) is a monomial term combining components of x at different powers, e.g., $x_1 x_2$, $x_1^2 x_2$, $x_1^2 x_2$ etc., $a = [a_1, a_2, \ldots, a_{Nt}]$ are the model parameters, and $N_t$ is the number of terms. To determine the machine-learning model parameters, a cost function is defined and optimized. Thus, the sum of squares is minimized, described by Equation (11):

$$C(a) = \sum_{i=0}^{N} (P(x_i) - y_i)^2 \quad (11)$$

With respect to the inputs xi, C(a) is a highly nonlinear function. However, with respect to the parameters of the machine-learning model, a is a quadratic function where the minimum may be computed directly by solving the normal equation of the over-determined linear system Pa=y. Equation (12) is employed for this purpose:

$$a = (P^T P)^{-1} P^T y \quad (12)$$

where P is a N by the N, matrix containing the numerical values obtained when evaluating each polynomial feature pi(x), i∈[1, N.] for each data sample $x_i$, i∈[1, N] (e.g. the resulting ciphertext values from act 105).

Although all the steps above require only algebraic operations, the proposed encoding scheme does not allow for the division of two numbers, such as $(P^T P)^{-1}$ in the encoded-encrypted form. Therefore, in act 107, the two matrices resulting from the dot products $(P^T P)$ and $P^T y$ are computed so that, based thereon the matrix P is generated.

With the combination of encoding and encryption, division of two encrypted-encoded values may be challenging. In one case, an additional encoding layer may be introduced by rewriting a real number as a fraction, and then encoding the numerator and denominator. However, the computational overhead may increase drastically. Furthermore, the additional operations may not guarantee a correct result because of the increasing growing noise inherent to some HE schemes. Accordingly, division may be avoided by decryption of the linear system.

Moving beyond division, calculating the inverse of an encoded and encrypted number may be challenging. Though the Newton-Raphson iterative method for solving 1/X-den=0 provides the inverse of the denominator, the correctness of the result is dependent on the initial approximation. As the underlying information is secret (e.g. encrypted), it is uncertain what initialization may guarantee convergence to the optimum value in a few iterations. Alternatively, because a comparison may not be performed between encrypted numbers, a standard or fixed number of iterations may be specified. However, specifying a set number of iterations for all cases may be prone to errors that occur because of an insufficient number of iterations, or because the plaintext domain was exceeded during computation. Considering the scenario of training a model on sensitive medical data, where confidentiality is crucial, but so is the accuracy of the model, the usage of such uncertain methods (that compute division on encoded-encrypted numbers) may be avoided in the direct optimization approach (e.g. by decrypting values prior to operations beyond multiplication, addition, and subtraction).

Because division my not be provided for encrypted data, encoded data, not encrypted-encoded data, the remaining operations of equation 12 are performed after decryption and decoding. In act 109, the matrix P is decrypted and decoded. The decryption may use the same HE encryption scheme as in act 105. Through decryption, the cost function may be solved to optimize the machine-learning model over the training data.

While the use of the cost function in equations (11) and (12) may prevent the model fitting process to be performed completely on encrypted data, in some cases, the number of data samples N is much larger than the number of model parameters $N_t$. Therefore, the dot product $(P^T P)$ results in a small matrix $N_t$ by $N_t$, while $P^T y$ results in a vector of size $N_t$. Since the input data are significantly regressed by these operations, decrypting does not expose the original data.

Referring to overfitting issues, they typically appear when the model is too complex. In our case, if the number of polynomial terms is not too large, the model does not attempt to learn or explain the random error or noise present in the data. Furthermore, overfitting may be addressed by using larger training datasets: the more samples are used for training, the more difficult it is for the model to learn the error or noise. Thus, according to [29], the number of samples should be at least 10-15 for each term in the model to avoid overfitting. In our use cases, this condition is met in all experiments, as the number of samples exceeds the required threshold (e.g., 9200 training samples for 80 features in the seizure detection use case).

In act 111, the parameters of the machine learning model are generated by solving equation (12) based on the matrix P. The parameters are in plaintext form because the input to equation (12) is, in this case, the plaintext data output from act 109. Having the parameters, the machine-learning model is a machine-learned model configured to accept as input data (e.g. the EEG signal) and output a result (e.g. a label) based on the input.

In some cases, the training data applied to the machine-learning model in act 113 is plaintext. For example, the training data may be a publicly available dataset for which there are no privacy concerns. By keeping the training data decrypted, time, energy, and money may be saved while training. In this case, the encryption act 105 may be omitted, and, accordingly, the decryption act 109 may also be omitted. However, the model trained to accept decrypted data may be deployed in the cloud or in another public environment where patient privacy may be protected.

In some other cases, the training data applied to the machine-learned model during training is encrypted and, as a result, the parameters of the model are configured to process encrypted data. A clinical environment may desire a local version of the machine-learned model. However, because the information input and retrieved from the model remains within the clinical environment, patient privacy is protected end to end. To save time, money, and energy, the locally deployed machine-learned model may be modified to accept and output decrypted data.

When the parameters of the machine-learned model are desired in plaintext form (e.g. for local deployment of the machine-learning model), the machine-learned model may be stored as in act 117, without the encoding and/or encryption in act 115.

In act 115, the plaintext (e.g. decoded and decrypted) parameters of the machine-learned model may be encrypted and/or encoded. Even in the case that the training data applied to the model is encrypted or decrypted, the parameters of the model may be "decrypted", so the model is configured to accept decrypted data as an input. However, the deployment environment may apply data to the model that is in a different encryption state than the training data or the resulted parameters. Accordingly, in act 115, the parameters may be encrypted or encoded depending on the deployment (or inference) environment.

In act 117, the machine-learned model is stored. For example, the model may be stored in the memory 705 of FIG. 7. In another example, the machine-learned model may be output (e.g. by the network adapter 707 of FIG. 7) to a server or the cloud. In one example, when act 117 proceeds from act 113, the machine-learned model is stored with plaintext parameter values. In another example, when act 117 proceeds from act 115, the machine-learned model is stored with encoded and/or encrypted parameter values.

Figure 2:
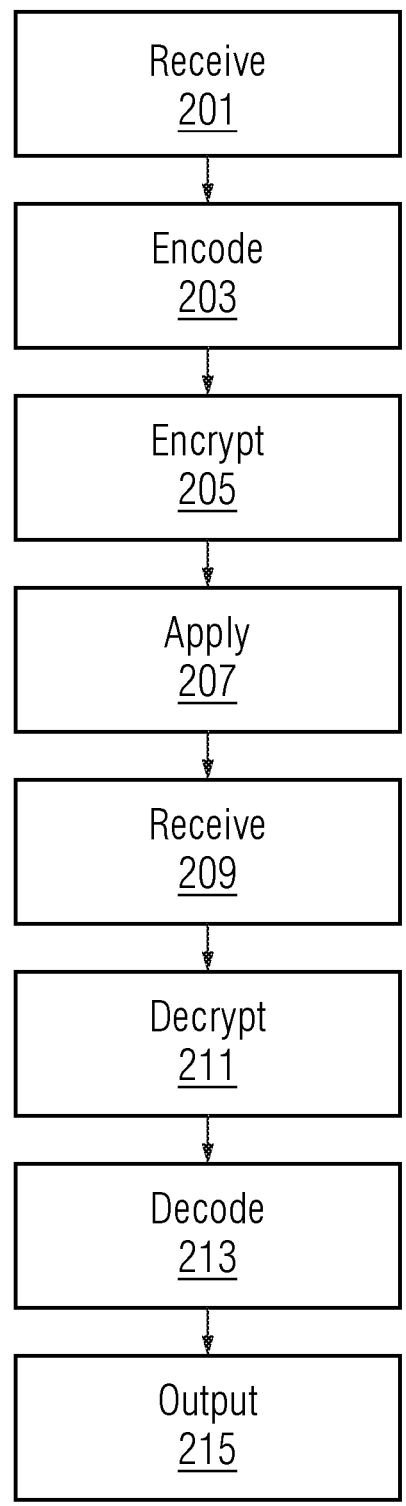
FIG. 2 illustrates an embodiment of a method of assessing medical images with a machine-learned model.

FIG. 2 illustrates an embodiment of a method of performing machine-learning tasks on medical data. More, fewer, or different acts may be performed. In some cases, acts 203 and 205 may be omitted. A processor coupled to a memory may be configured to perform one or more of the acts. For example, the processor 703 of FIG. 7 may be configured to perform one or more of the acts of FIG. 2. One or more acts of FIG. 2 may proceed from the acts of FIG. 1. For example, act 201 may proceed from act 117 of FIG. 1.

In act 201, input data is received. The input data may include data recorded from a medical device, such as EEG data. The medical device 709 of FIG. 7 may generate the input data. The data may be received directly from the medical device or through one or more intermediaries. In some cases, the medical data is received from the medical device or a computer over a network. In some other cases, the medical data is stored and later received. For example, a server may store medical data and send or load the medical data for machine learning tasks.

In some cases, the received input data may already be encoded and/or encrypted. In such cases, act 203 and/or act 205 may be omitted, respectively.

In act 203, the input data is encoded. The encoding scheme used to encode the input data may represent a value (e.g. a real or rational number) as a sequence of small integers, so that each polynomial term comprises a sub-unity number multiplied by a (e.g. negative) power of ten. The polynomial may encrypt negative numbers by expressing each coefficient of the polynomial as a difference. Further, null digits in the value may be ignored, removed, canceled, or otherwise unencoded in the sequence of polynomial terms. Once encoded, the input data may be referred to as encoded input data.

Based on a required precision for the application of the machine-learned model (e.g. classification, segmentation, simulation), the number of terms in the sequence may be set. A precision parameter specifying the number of terms may be received along with the input data (e.g. in act 201) or separately.

When the precision is not predetermined, the precision for the encoding may be determined. Though it may be difficult to determine the number of terms required to ensure no loss in accuracy based on the input data dimensionality, the precision parameter also depends on the initial precision of the numbers contained in the input data. While increasing values of n may result in increasing precision of the results, the runtime for computations on the data may greatly increase. However, the total number of operations performed on encoded and encrypted data may be determined from just the number of training samples:

$$N_{op} = 2sf(f+1) \tag{13}$$

where s is the number of training samples and f is the number of features. The computational time may also be predicted based on the number of training samples s and the number of encoding terms n by computing:

$$T = T_{ad}\frac{N_{op}}{2}n + T_{mul}\frac{N_{op}}{2}n^2 \tag{14}$$

where $T_{ad}$ and $T_{mul}$ denote the average time in seconds required for an addition or a multiplication operation between two encrypted coefficients of the polynomial representation. The value of T is also expressed in seconds.

To determine the value of the precision parameter, an analysis may be performed locally (e.g. at the clinical site). Specifically, an approximated training runtime for ensuring no loss in accuracy may be estimated empirically.

In act 205, the encoded input data is encrypted. A result of the encryption is encrypted input data. The encryption may use a HE scheme. The HE scheme used preserves the ability to perform addition and multiplication on the encoded data (e.g. on the ciphertext). Because the encoding represents negative numbers as a series of polynomials, subtraction of values may be performed using an HE scheme explicitly supporting addition. Further, because the encoding represents real and rational numbers as a series of integers, an HE scheme only be capable of performing operations on small integers may be used. Additionally or alternatively, a HE scheme may be used that preserves the ability to perform scalar operations. Scalar operations may be preserved to allow for operations on the input data when the machine-learned model may be trained on training data encrypted with a first key, and the input data is encrypted with a second key different from the first key. Once encrypted, the input data may be referred to as encrypted input data or encoded-encrypted input data.

In act 207, the encrypted input data is applied to a machine-learned model. The machine-learned model may be trained on another set of encrypted-encoded input data to take as input encrypted data and output an encrypted result (e.g. a label of the input data).

In one case, the machine-learned model may be based in a cloud. For example, a cloud environment may be suitable for developing machine learning based models for various prediction tasks based on sensitive data. By the encryption process of act 205, the data sent to the machine-learned model in the cloud is protected. Alternatively, the machine-learned model may be based locally, for example, on an internal network In act 209, an encrypted result is received from the machine-learned model. The result may be received, for example, over a network connection. Because the input to the machine-learned network is encrypted (and, in this case, because the machine-learned network does not have a decryption key or ability to decode the input), the output data is encrypted with the same HE scheme as the input.

The received result may be the outcome of the machine-learning task performed on the input data. For example, when the machine-learning task is classification, the machine-learned model may, based on an input signal or image, output a label for the signal or image. Additionally or alternatively, the result may include a segmentation, a classification, a registration, a quantification, a fusion image, and/or a simulation.

In act 211, the encrypted result is decrypted according to the HE scheme (e.g. the scheme used in act 205). After decryption, a plaintext (but encoded) result is obtained.

In act 213, the encoded result is decoded. The decoding converts the result from a series of polynomial terms to a real or rational number. In the example of a label, the value of the result may correspond to a particular word label, such as the presence or absence of a seizure.

In act 215, the result is output. The result may be output with the input data. The result and input data may be output to a display, for example, the display 711 of FIG. 7. Additionally, or alternatively, the result and/or input data may be output to memory, such as the memory 705 of FIG. 7.

The performance of machine-learned model operating on encoded and encrypted data may be compared to performance on plaintext operations to measure speed and accuracy.

In one example, synthetic, randomly generated data is used to compare operations on encrypted-encoded data and operations on plaintext. The data may be encoded using the polynomial representation and encrypted using a HE scheme capable of addition and multiplication of small integers. The experiments included performing a multivariate linear regression with different data sizes. A matrix X contains random data samples in the [0, 1] interval, and a corresponding random output vector y. Computation of the regression coefficients or parameters proceeded, for example, as described with respect to FIG. 1.

The following metrics were analyzed as a function of data size: run time, the magnitude of the resulting values, and the number of arithmetic operations performed. The magnitudes of the values and the number of operations are important because many HE schemes operate on only a fixed range of integer values. Performing operations on encrypted (and therefore unknown) values may result in values becoming too large, thus exiting the range beyond which valid results are obtained. While the magnitude of values may not be determined in some cases, with synthetic data, the magnitude range of the input values and the total number of operations are known.

To study the impact of the number of features, the number of samples may be fixed (500 samples), and the number of features may be varied between 2 and 102. To study the influence of the number of samples, the number of samples may be varied from 15 to 19,915 while the number of features may be fixed (two features). In both cases, for consistency, during this analysis, the precision parameter (e.g. the number of terms in the polynomial representation) may be set to 20, and a 256-bit encryption key may be used.

Figure 3:
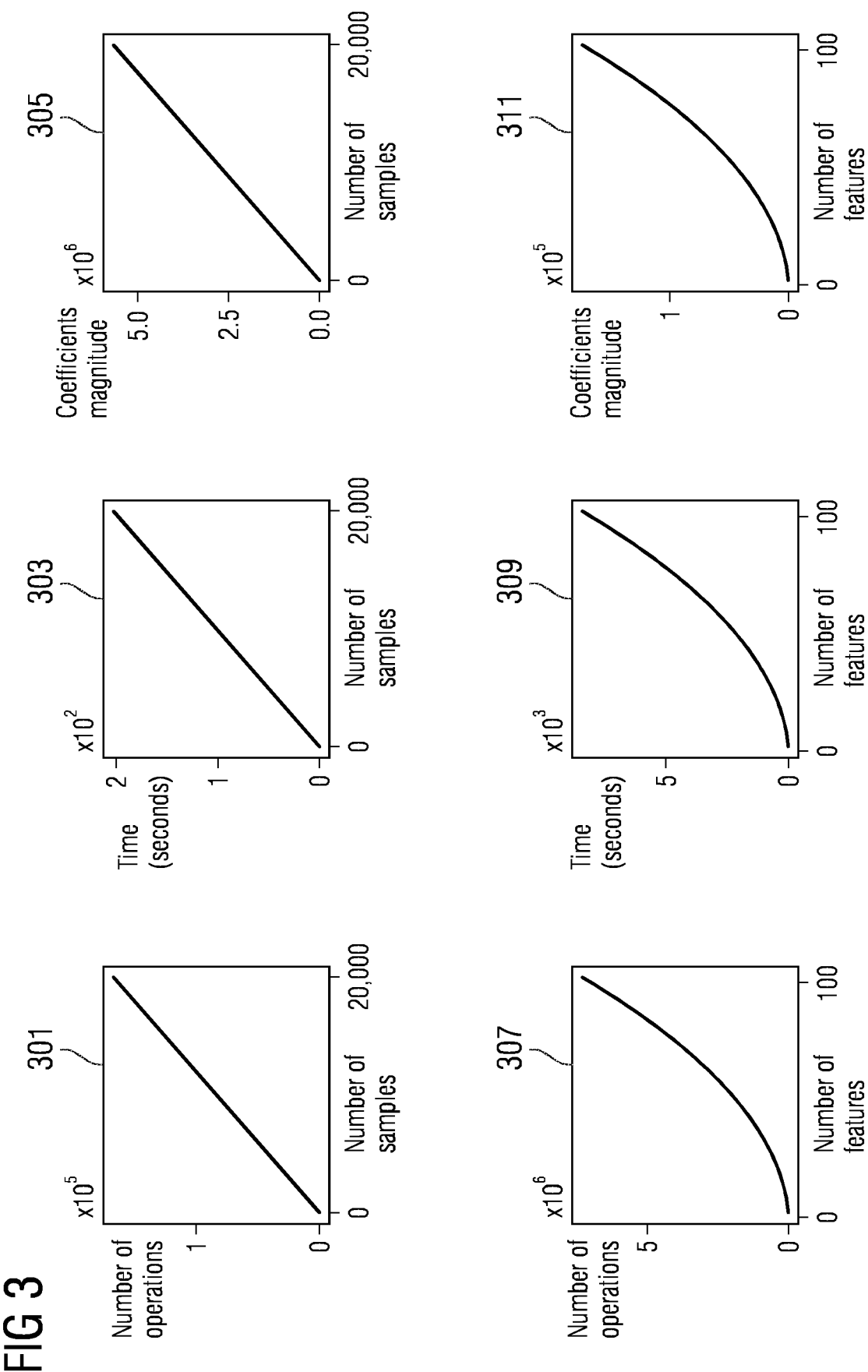
FIG. 3 illustrates example operational performance metrics as a function of input data size.

FIG. 3 illustrates the values of the run time (303, 309), the magnitude of the resulting values (305, 311), and the number of arithmetic operations performed (301, 307) as a function of the data size (samples or features). An increasing number of features has an exponential impact on the number of operations, the computational time, and on the ciphertext size, while an increasing number of samples affects the number of operations, computational time, and the ciphertext size linearly. A similar conclusion applies to the maximum magnitude of the polynomial coefficients obtained as a result. Although the computational time is increased, the proposed encryption-encoding method may be used on data sizes of real-world proportions.

To analyze the prediction error between the plaintext and ciphertext operations, the mean absolute error and the root-mean-square error for all experiments may be calculated. The error is defined as the difference between the outputs obtained, using plaintext and ciphertext values. The error may be close to zero (in double precision). However, as the encoding method is limited by the precision parameter, a large error value versus plaintext operations may indicate that the precision parameter is too small for a certain application.

Figure 4:
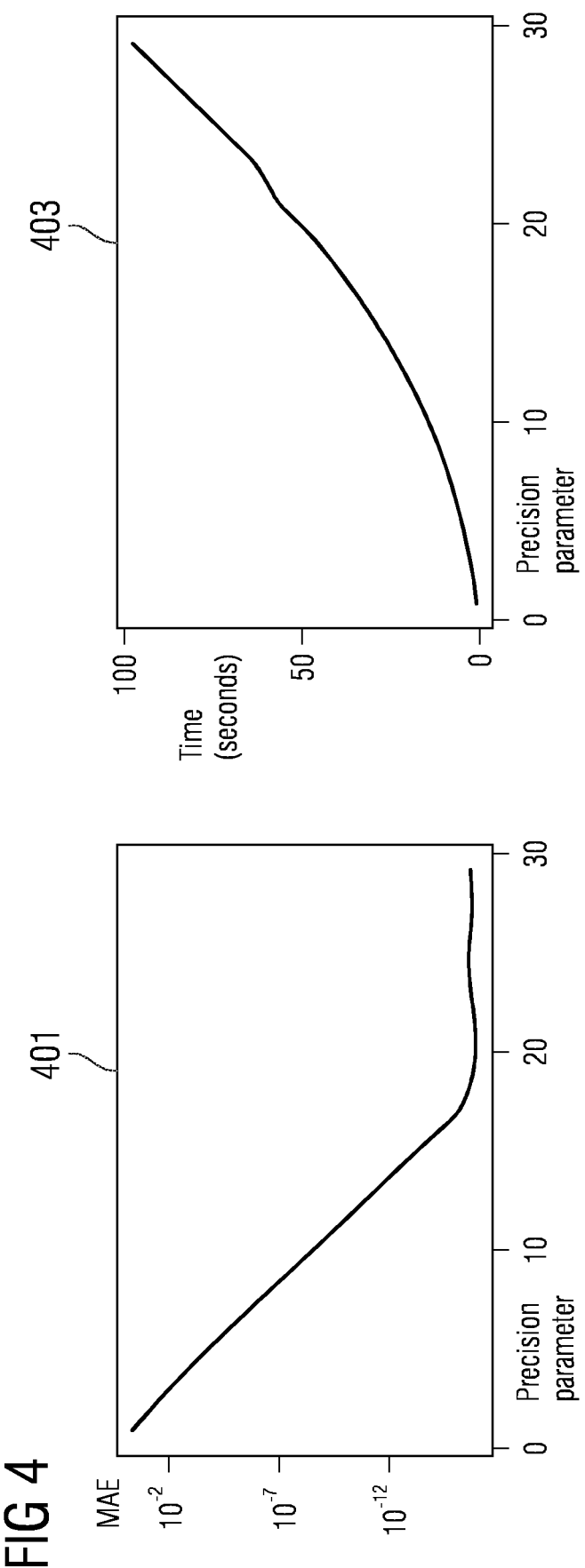
FIG. 4 illustrates example metrics for operations on encoded data.

FIG. 4 illustrates error (401) and computational time (403) metrics for plaintext and ciphertext operations. A randomly generated dataset with 1000 samples and 5 features may be used for all experiments illustrated in FIG. 4. To determine the dependence between the number of terms in the polynomial encoding (e.g. the precision parameter), the numerical error, and the execution time, the same experiment may be run multiple times while varying the precision parameter from 1 to 30. As shown in FIG. 4, there may be a trade-off between the accuracy (401) and computational time (403): an increase in the number of terms used for the encoding leads to a significant decrease in error (MAE), but with a cost in terms of the computational time.

The encryption-encoding scheme may be used for a clinical task, such as using an EEG signal to diagnose a seizure or to determine a predisposition to alcohol.

For seizure detection, the encryption-encoding scheme may be used to determine if an epileptic seizure activity occurred during an EEG recording. An input sample contains a sequence of real numbers representing an EEG signal, which may encompass surface recordings from healthy individuals (with their eyes closed or open) or intracranial recordings from epilepsy patients (during the seizure-free interval or epileptic seizures) from different brain areas. A 128-channel amplifier system may be used to record all EEG signals.

The original dataset contains 500 files, each of them corresponding to 23.6 s of EEG recording of one individual, at a sampling rate of 173.61 Hz. Each file represents a single-channel EEG segment that may be selected from continuous multichannel EEG recordings.

Each time sequence contains 4097 EEG values equally sampled in time. A dataset was used where every recording may be split into 23 chunks corresponding to 1 s of recording, consisting of 178 data points each. The resulting dataset contains 11,500 samples. The models are evaluated using five-fold cross-validation: the dataset may be divided into five folds, each with 2300 samples, leading to 9200 training samples and 2300 testing samples for each experiment. A ground truth label is associated with each EEG recording: 1—epileptic seizure activity, 2—tumor area, 3—healthy brain area of a patient with an identified tumor, 4—the patient had their eyes closed during recording, and 5—the patient had their eyes open during recording.

A binary classification problem is defined by considering that all recordings labeled as 2, 3, 4 or 5 indicate the absence of an epileptic seizure (ground truth label 0), while ground truth label 1 indicates the presence of an epileptic seizure. The resulting dataset is imbalanced because only 20% of the recordings have a class label of 1 (epileptic seizure recorded). Because the experiments employ a linear model, the class imbalance is offset by setting the threshold used to discretize the output closer to 0. Hence, all samples with an output value greater than 0.1 are classified as class 1. Input data are normalized in the range [−1, 1].

Figure 5:
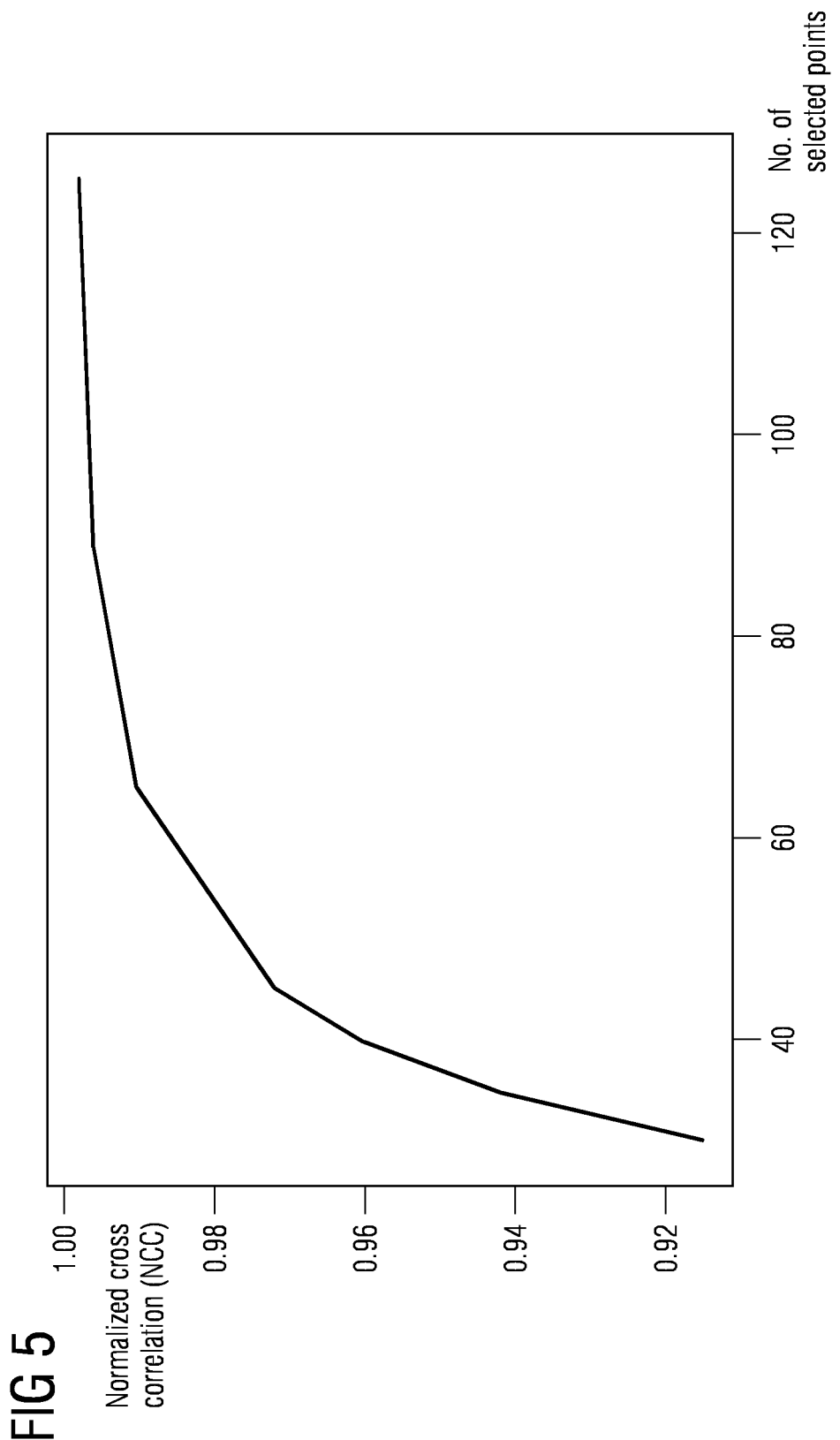
FIG. 5 depicts an example plot of cross-correlation.

Because, in the case of an EEG, all the features of an input sample represent a time sequence, the original signal of each entry may be down-sampled through interpolation to reduce the complexity of the problem. For example, A one-dimensional linear interpolation may be used. Normalized cross-correlation (NCC) may be computed between the initial and the resampled signal to evaluate the impact of the interpolation operation and is shown in FIG. 5. Thus, a trade-off may be present between the model complexity and loss of information. In one case, it may be suitable to use the resampled signal with the minimum number of data points and with an NCC value greater than 0.95. These conditions specify 40 data points for the down-sampled signal.

Figure 6:
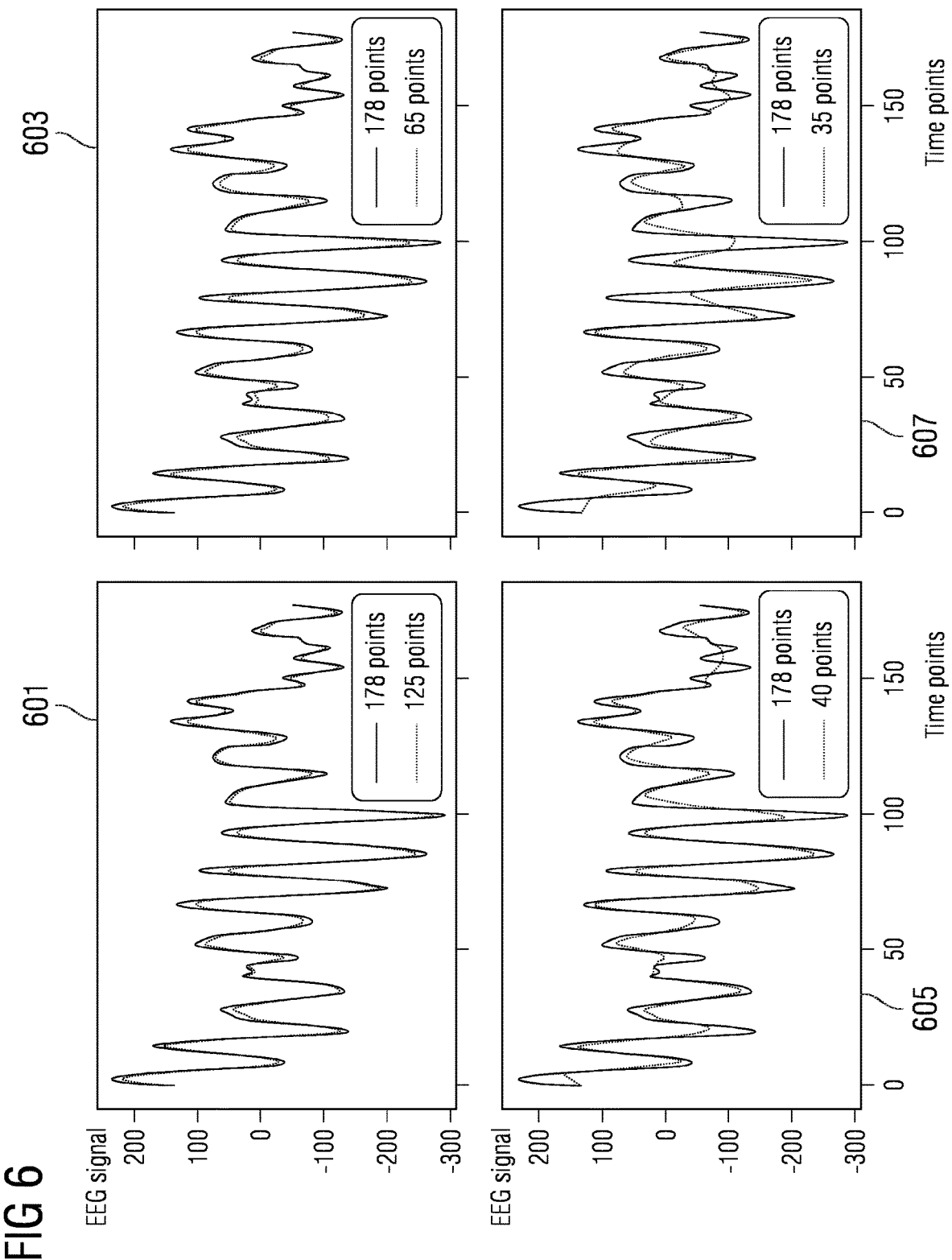
FIG. 6 illustrates multiple example EEG signals.

Considering the restructured version of the dataset, where 178 points correspond to 1 s of the recording, and the down-sampled signal (40 points for 1 s), the frequency may be reduced from 178 Hz to 40 Hz. A comparison between the original EEG signal and some down-sampled versions is illustrated in FIG. 6. The same EEG signal at 178 sample points is compared to four different down-sampling rates. Plot 601 shows a comparison to 125 points, plot 603 shows a comparison to 65 points, plot 605 shows a comparison to 40 points, and plot 607 shows a comparison to 35 points.

To test the ability of the encryption-encoding scheme to detect seizures, multiple experiments were run with different input data configurations. In a first case, all 178 initial data points are used in each sample as input. In a second case, all 178 initial data points are used in each sample with the 178 corresponding quadratic terms (356 features overall). In a third case, a down-sampled version of each sample is used. The number of data points was gradually reduced from 178, and the mean NCC over the entire dataset was computed for each down-sampled version. As discussed above and as shown in FIG. 5, the down-sampled version with the smallest number of data points for which the average NCC was still larger than 0.95 had 40 features (instead of the initial 178). When the corresponding quadratic terms were added, a total of 80 features were present per sample. FIG. 5 displays the variation of the mean NCC as a function of the number of samples. FIG. 6 displays, for one EEG signal, the original sample, and the resampled sample for different numbers of data points.

For all three input data configurations, the experiments were first conducted using the plaintext data: both a multivariate polynomial regression and an SVM model were evaluated, using five-fold cross-validation. The optimal values of the SVM parameters were determined by performing a grid search. For this use case, the best results were obtained for v=0.3 and C=1. Thus, by setting v=0.3, it is probable that, at most, 30% of the training samples are allowed to be wrongly classified and at least 30% of them act as support vectors.

Table 1 displays the classification metrics aggregated over all five folds: accuracy, sensitivity, specificity, positive predictive value, negative predicted value. For each of the five folds, the metrics were computed only on the testing subset. While the support vector machine (SVM) model is largely independent of the input data configuration, the performance of the polynomial regression (PR) model increases significantly both when adding the quadratic terms and when reducing the number of data points per sample (increase in performance stems mainly from an increase in sensitivity). It may be understood from the performance obtained using SVM, before and after down-sampling the signal, that the pre-processing step does not influence the classification process.

For the last input data configuration (80 features) the polynomial regression model was also trained on ciphertext values, considering the encoding precision parameter equal to 35 and a 256-bit encryption key. The results were identical down to double precision when compared to the plaintext experiment. The precision parameter for this use case was chosen based on the synthetic data results. As the quadratic resampled dataset has a larger number of features (80 compared to 5) and training samples (9200 compared to 1000), to ensure no loss in performance, the precision parameter was chosen to be equal to 35, which is larger than the values used in the synthetic data experiments displayed in FIG. 4.

In terms of computational time, a comparison between the plaintext and ciphertext polynomial regression experiments is displayed in Table 2. In both training and inference, the time increases for encrypted version; however, inference time still remains in the order of milliseconds. For the parallelized version, 4 processes were employed, and experiments were run on a machine equipped with an Intel Core i7 CPU running at 4.2 GHz and 32 GB RAM at 2666 MHz.

TABLE 1

Performance comparison when using different input data configurations
in the EEG-based seizure detection use case.

|  | Initial data 178 features | | Quadratic data 356 features | | Resampled data 80 features | | |
| --- | --- | --- | --- | --- | --- | --- | --- |
|  | PR | SVM | PR | SVM | PR plaintext | PR ciphertext | SVM |
| Accuracy | 80.59 | 95.78 | 89.22 | 95.86 | 92.26 | 92.26 | 95.85 |
| Sensitivity | 34.25 | 98.82 | 84.40 | 98.60 | 86.56 | 86.56 | 98.70 |
| Specificity | 92.17 | 95.02 | 90.43 | 95.17 | 93.68 | 93.68 | 95.14 |
| PPV | 52.46 | 83.23 | 68.81 | 83.62 | 77.44 | 77.44 | 83.54 |
| NPV | 84.86 | 99.69 | 95.86 | 99.63 | 95.54 | 95.54 | 99.65 |

In terms of computational time, a comparison between the plaintext and ciphertext polynomial regression experiments is displayed in Table 2. For both training and inference, the time increases for the encrypted version. However, the inference time remains in the order of milliseconds. For the parallelized version, four processes were employed.

TABLE 2

Training and inference runtime comparison between
plaintext and ciphertext implementation versions
for the seizure detection use case.

|  | Plaintext | Ciphertext | Ciphertext Parallelized |
| --- | --- | --- | --- |
| Training runtime/fold | 0.0119 s | 23.60 h | 7.05 h |
| Inference runtime/sample | $1.73 \times 10^{-6}$ s | 0.012 s | |

Considering the scenario where the model is used only on ciphertext data, without any previous analysis regarding its performance, the precision parameter is large enough (35 powers or terms) to ensure zero loss in accuracy. This led to the same results as those obtained on plaintext data, but the runtime was significantly larger. The influence of choosing a lower precision parameter may be determined from multiple experiments and analysis of the computational time and performance loss. As displayed in Table 3, the runtime may be improved by choosing a smaller number of terms for the encoding step, but after a certain threshold is exceeded (21 powers for this use case), the performance decreases.

TABLE 3

Influence of the precision parameter on the loss
of accuracy and on the computational time for
the EEG-based seizure detection use case.

|  | Precision Parameter (Number of Terms) | | | | | | |
| --- | --- | --- | --- | --- | --- | --- | --- |
|  | 35 | 32 | 29 | 26 | 23 | 21 | 20 |
| Loss in accuracy | 0 | 0 | 0 | 0 | 0 | 0 | 1.66 |
| Runtime/fold (hours) | 7.05 | 6.02 | 4.69 | 3.89 | 2.97 | 2.41 | 2.16 | task—determining a predisposition to alcoholism. EEG signals may provide valuable information for the analysis of the predisposition to alcoholism, based on the differences between the frequency bands of alcoholic and non-alcoholic individuals. A dataset was collected during a study evaluating the correlation between EEG signals and genetic predisposition to alcoholism. The signals were measured by 64 electrodes scanned at 256 Hz (3.9 ms epoch) for 1 s. The sensors were placed on the subjects' scalps according to the International 10-20 standard. The subjects were exposed to one stimulus (S1) or two stimuli (S1 and S2) represented by pictures. The two stimuli were shown in a matched condition (S1 was identical to S2) or in a non-matched condition (S1 differed from S2).

The dataset is split into two folders—train and test—each of them containing 10 runs for 10 alcoholic and 10 nonalcoholic subjects. The folders consist of trails files with the following columns: trial number, sensor position, sample number, sensor value, subject identifier, matching, channel number, name, and time. In a single trial run, a patient provides 256 samples for each of the 64 electrodes. The pre-processed training dataset contains 153,600 samples of 64 features corresponding to the 64 electrodes. The corresponding ground truth labels are 0 if the subject is non-alcoholic and 1 if the subject is alcoholic. The pre-processed testing dataset also contains 153,600 samples of 64 features and the ground truth label. The input data are normalized in the range [−1, 1].

Based on the fact that the dataset consists of 153,600 samples of 64 features corresponding to the 64 electrodes, the ground truth labels, and that the computational time required for an experiment on the ciphertext data increases considerably once the number of samples becomes larger than 10,000, a balanced subset of 10,000 samples of the data was selected.

Four experiments were performed on plaintext data: 1.) The machine learning models were trained on the original dataset (153,600 samples and 64 features). 2.) The machine learning models were trained on 10,000 balanced samples. The number of features was unchanged at 64. This is the baseline experiment to be conducted also on the ciphertext data (experiment 1 may not be run on ciphertext since the number of samples is too large). 3.) The machine learning models were trained on the entire dataset (153,600 samples) and all polynomial combinations of features with degrees less than or equal to 2 were considered, leading to a total of 2145 features. The idea is to determine whether increasing the model complexity leads to better performance. Due to the large number of features, it is not feasible to run this experiment on ciphertext data. 4.) The machine learning models were trained on 10,000 balanced samples with 128 features (the original 64 and their quadratic terms). Considering the computational overhead introduced by the encoding and encryption steps, this design may represent a suitable trade-off solution.

For the plaintext experiments, the SVM approach was used. The parameters of the SVM classifier that led to the best performance were obtained through a grid search (n=0.5 and C=1). In Table 4, the classification results for samples representing individual time points, recorded by the 64 electrodes at a given moment are shown. All reported metrics were computed using only the testing dataset. The columns represent the results of the experiments described above, where the input was normalized in the range [−1, 1]. Because in 4.), only some of the polynomial combinations of features are used (the original and quadratic features) and the training is performed on only the 10,000 samples subset from 2.), the accuracy is increased when compared to 1.) (original dataset), and the computational cost is significantly reduced compared to 3.). While adding the quadratic terms improves the performance of the polynomial regression algorithm, the SVM algorithm leads to similar performance for 2.) and 4.).

TABLE 4

Performance comparison when using different input data configurations in the EEG-based predisposition to alcoholism detection use case.

|  | $E_1$ (153,600, 64) | | $E_2$ (10,000, 64) | | $E_3$ (153,600, 2145) | | $E_4$ (10,000, 128) | | |
|---|---|---|---|---|---|---|---|---|---|
|  | PR | SVM | PR | SVM | PR | SVM | PR Plain Text | PR Ciphertext | SVM |
| Accuracy | 57.34 | 87.46 | 57.27 | 79.33 | 83.92 | 84.27 | 68.52 | 68.52 | 79.08 |
| Sensitivity | 57.26 | 89.06 | 61.20 | 80.15 | 83.81 | 83.97 | 68.45 | 68.45 | 79.22 |
| Specificity | 57.43 | 85.86 | 53.35 | 78.51 | 84.03 | 84.57 | 68.59 | 68.59 | 78.94 |
| PPV | 57.35 | 86.30 | 56.74 | 78.86 | 84.00 | 84.48 | 68.55 | 68.55 | 79.00 |
| NPV | 58.85 | 88.70 | 57.90 | 79.82 | 83.85 | 84.07 | 68.49 | 68.49 | 79.16 |

For the results in Table 5, a voting scheme is applied to determine a single prediction per patient (alcoholic or non-alcoholic): the outputs of all samples corresponding to a patient (which form a time series) are used as input to the voting scheme, where each sample has the same weight.

TABLE 5

Performance comparison when using different input data configurations in the EEG-based predisposition to alcoholism detection use case after applying the voting scheme.

|  | $E_1$ (153,600, 64) | | $E_2$ (10,000, 64) | | $E_3$ (153,600, 2145) | | $E_4$ (10,000, 128) | | |
|---|---|---|---|---|---|---|---|---|---|
|  | PR | SVM | PR | SVM | PR | SVM | PR Plain Text | PR Ciphertext | SVM |
| Accuracy | 59.66 | 96.66 | 60.16 | 94.16 | 95.50 | 93.66 | 79.83 | 79.83 | 96.16 |
| Sensitivity | 63.00 | 98.00 | 65.33 | 95.66 | 97.33 | 95.33 | 77.66 | 77.66 | 97.66 |
| Specificity | 56.33 | 95.33 | 55.00 | 92.66 | 93.66 | 92.00 | 82.00 | 82.00 | 94.66 |
| PPV | 50.06 | 95.45 | 59.21 | 92.88 | 93.89 | 92.25 | 81.18 | 81.18 | 94.82 |
| NPV | 60.35 | 97.94 | 61.33 | 95.53 | 97.23 | 95.17 | 78.59 | 78.59 | 97.59 |

In Table 6, the runtime for both inference and training are displayed. The runtime increases when processing encrypted data but remains reasonably small for the inference step.

TABLE 6

Training and inference runtime comparison between plaintext and ciphertext versions in the EEG-based predisposition to alcoholism detection use case.

|  | Plaintext | Ciphertext | Ciphertext Parallelized |
|---|---|---|---|
| Training | 0.0286 s | 59.69 h | 32.28 h |
| Inference | $3.46 \times 10^{-6}$ s | 0.018 s | |

A decreasing tendency in the runtime is shown in Table 7, but the minimum number of terms required for zero loss in performance is smaller than in the example where seizures were detected. Although the number of operations is larger, the initial precision of the training data is also reflected in the encoding precision.

TABLE 7

Influence of the precision parameter on the loss of accuracy and on the computational time in the EEG-based predisposition to alcoholism detection use case.

| | Precision Parameter (Number of Terms) | | | | | | | |
|---|---|---|---|---|---|---|---|---|
| | 35 | 32 | 29 | 26 | 23 | 20 | 17 | 14 |
| Loss in accuracy | 0 | 0 | 0 | 0 | 0 | 0 | 0 | 0.41 |
| Runtime (hours) | 32.28 | 26.53 | 22.17 | 17.91 | 13.02 | 10.90 | 8.16 | 5.75 |

Figure 7:
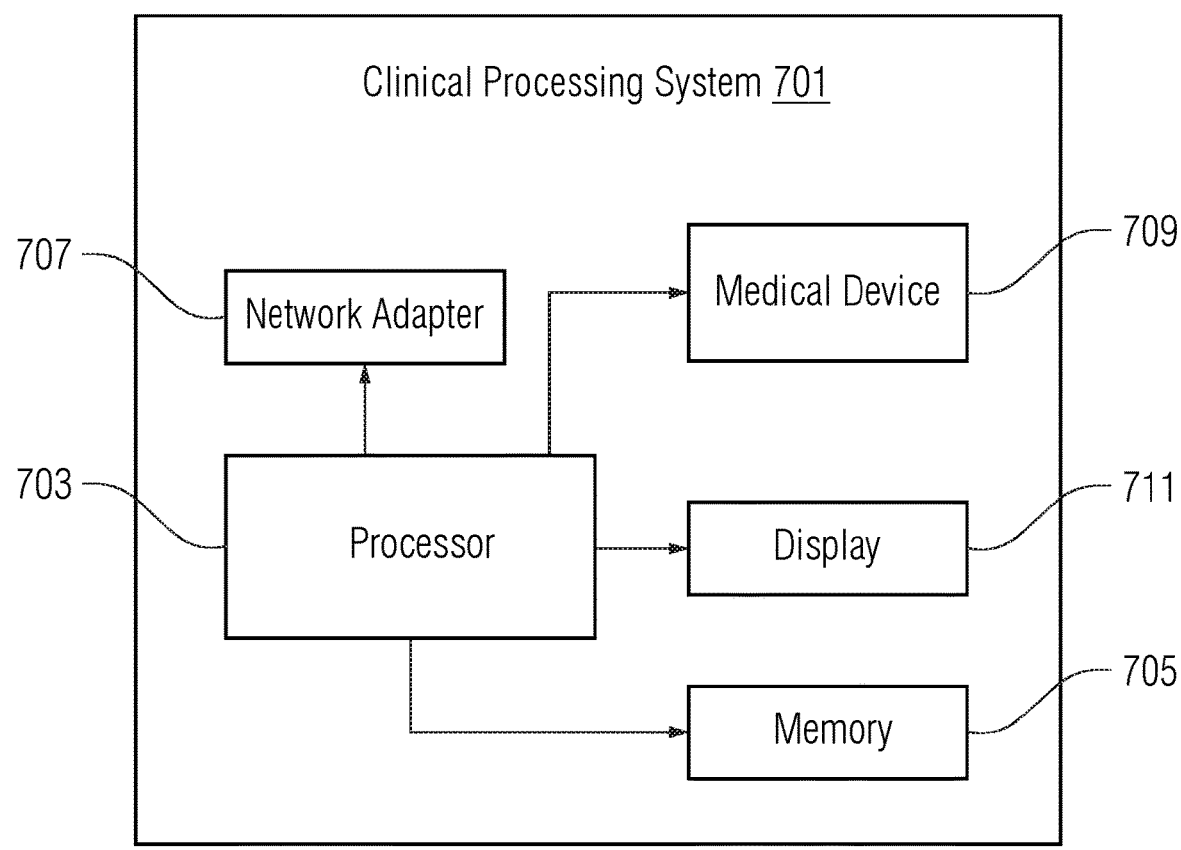
FIG. 7 is a block diagram of one embodiment of a clinical assessment system.

FIG. 7 is a block diagram of one embodiment of a medical image processing system. The clinical processing system 701 may include an image processor 703 coupled with a memory 705 and in communication with a network adapter 707, a medical imaging device 709, and a display 711.

The clinical processing system 701, including one or more components 703-711 of the clinical processing system 701, may be configured to perform one or more of the acts of FIG. 1, FIG. 2, or other acts. The clinical processing system 701 may be implemented in one or many different forms. For example, the clinical processing system 701 may be implemented as a desktop computer program, a server based computer program, a mobile application, a cloud based service, or otherwise.

The processor 703 may be a general purpose or application specific processor. The processor 703 may be configured to or may execute instructions that cause the processor 703 to receive data, such as medical data and/or medical data results. The processor may receive the data via the network adapter 707, from the memory 705, from the medical device 709, or from another device. The data may be generated by a medical system or device. For example, the medical device 709 or another medical device or system may generate the medical data. The processor 703 may be further configured to apply the medical data and/or auxiliary data to a machine-learned model. The machine-learned model may be stored in the memory 705. In some cases, the machine-learned model may be received at the processor 703 via the network adapter 707. In some cases, the processor 703 may be configured to train the machine learning model. For example, the processor 703 may be configured to train the model according to FIG. 3. The processor 703 may be further configured to generate medical data results based on applying the medical data to the machine-learned model. The processor 703 may be further configured to output the labels and/or medical data results.

The memory 705 may be a non-transitory computer readable storage medium. The memory 705 may be configured to store instructions that cause the processor to perform an operation. For example, the memory 705 may store instructions that, when executed by the processor 703, cause the processor 703 to perform one or more acts of FIG. 1, FIG. 2, or other acts. The memory 705 may be configured to store medical data, machine-learned models, or other information. The instructions for implementing the processes, methods, and/or techniques discussed herein are provided on non-transitory computer readable storage media or memories, such as a cache, buffer, RAM, removable media, hard drive, or other computer readable storage media. Non-transitory computer readable storage media include various types of volatile and nonvolatile storage media.

The network adapter 707 (e.g. a gateway) may be a software module executed by the processor 703. In some cases, the adapter may be implemented by a separate processor or by standalone hardware. The adapter 707 may be configured to receive and/or transmit medical data machine-learned models, or other information between components of the clinical processing system 701 and other components or systems. For example, the network adapter 707 may be in communication with a computer, a server, a medical device, or other devices.

The medical device 709 may be configured to generate medical data. The medical device may use an MR, CT, x-ray, EEG, or another modality to generate images or other data. The medical device 709 may be configured to send the medical data to one or more of the components of the clinical processing system 701. For example, the medical device 709 may send the images to the processor 703, the memory 705, the network adapter 707, or the display 711 directly or through one or more intermediaries.

The display 711 may be configured to accept user input and to display audiovisual information to the user. In some cases, the display 711 may include a screen configured to present the audiovisual information. For example, the display 711 may present the medical image data and/or the medical image result. Via the display 711, users may review the medical image result to assess whether the result is correct for the medical image data. The display 711 may include a user input device. For example, the display may include a keyboard, mouse, and/or a virtual or augmented reality environment. In some cases, the user may input information relating to the auxiliary information.

While the invention has been described above by reference to various embodiments, it should be understood that many changes and modifications may be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for performing machine-learning tasks on medical data, the method comprising:
   receiving, by a processor, medical data;
   encoding, by the processor, the medical data into encoded medical data according to an encoding scheme, wherein the encoding scheme represents a number in the medical data as a series of polynomial terms, wherein each polynomial term comprises a sub-unity number and a negative power of ten;
   encrypting, by the processor, the encoded medical data into encrypted medical data according to a homomorphic encryption scheme;
   applying, by the processor, the encrypted medical data to a machine-learned model, the machine learned model trained on second medical data;
   receiving, by the processor, an encrypted result generated by the machine-learned model based on applying the encrypted medical data to the machine-learned model;
   decrypting, by the processor, the encrypted result to an encoded result according to the homomorphic encryption scheme;
   decoding, by the processor, the encoded result to a medical data result according to the encoding scheme; and
   outputting, by the processor, the medical data result.

2. The method of claim 1, wherein the machine-learned model is cloud-based.

3. The method of claim 1, wherein a rational number is represented as the series of polynomial terms by the encoding scheme.

4. The method of claim 1, wherein negative numbers in the medical data are represented by a difference between two polynomial terms.

5. The method of claim 1, wherein null digits of the number are unencoded by the encoding scheme.

6. The method of claim 1, further comprising:
   receiving, by the processor, a precision parameter,
   wherein a number of the series of polynomial terms is based on the precision parameter.

7. The method of claim 1, wherein the medical data is encrypted with a cryptographic key used to encrypt the second medical data.

8. A method of training a machine-learning model, the method comprising:
   receiving, by a processor, training data comprising medical data and result data, wherein the medical data is annotated with corresponding result data;
   encoding, by the processor, the training into encoded training data according to an encoding scheme, wherein the encoding scheme represents a rational number as a series of polynomial terms, wherein each polynomial term comprises a sub-unity number and a negative power of ten;
   encrypting, by the processor, the encoded training data into encrypted training data according to a homomorphic encryption scheme;
   training with machine learning, by the processor, the machine-learning model based on the encrypted training data, wherein a result of the training is a machine-learned model configured to accept as input medical data and output result data, and wherein training further comprises:
      generating, by the processor, two matrices based on the encrypted training data;
      generating, by the processor, parameters of the machine-learning model based on the two matrices and a cost function comprising a linear system; and
   storing, by the processor, the machine-learned model.

9. The method of claim 8, further comprising:
   encoding, by the processor, the parameters of the machine-learning model into encoded parameters,
   wherein the machine-learned model is stored with the encoded parameters.

10. The method of claim 9, wherein the homomorphic encryption scheme includes processing scalar operations.

11. The method of claim 9, wherein a result of the training is a machine-learned model configured to accept as input encrypted medical data and output encrypted result data.

12. The method of claim 9, wherein the training data is aggregated into a matrix form.

13. The method of claim 8, further comprising:
   receiving, by a processor, the medical data;
   encoding, by the processor, the medical data into encoded medical data according to the encoding scheme;
   encrypting, by the processor, the encoded medical data into encrypted medical data according to a homomorphic encryption scheme;
   applying, by the processor, the encrypted medical data to the machine-learned model;
   receiving, by the processor, encrypted result generated by the machine-learned model based on the encrypted medical data sent to the machine-learned model;
   decrypting, by the processor, the encrypted result to an encoded result according to the homomorphic encryption scheme;
   decoding, by the processor, the encoded result to a medical data result according to the encoding scheme; and
   outputting, by the processor, the medical data result.

14. The method of claim 13, wherein parameters of the machine-learned model, the encrypted medical data, and the encrypted training data are encrypted with the same encryption key.

15. The method of claim 13, wherein parameters of the machine-learned model are encoded according to the encoding scheme,
   wherein the encrypted medical data is encrypted with a first key, and
   wherein the encrypted training data is encrypted with a second key different from the first key.

16. A clinical processing system, the system comprising:
   a processor, coupled with a memory containing instructions that, when executed, cause the processor to: send encoded-encrypted numerical data to a machine-learned model, wherein the encoded-encrypted numerical data is encoded according to an encoding scheme, wherein the encoding scheme represents a rational number as a series of polynomial terms, wherein each polynomial term comprises a sub-unity number and a negative power of ten; receive an encoded-encrypted result generated by the machine-learned model based on the encoded-encrypted numerical data sent to the machine-learned model; decrypt the encoded-encrypted result to an encoded result according to a homomorphic encryption scheme; decode the encoded result to a numerical data result according to the encoding scheme; and output the numerical data result to the memory.

\* \* \* \* \*